United States Patent [19]

Herrick

[11] Patent Number: 4,768,498

[45] Date of Patent: Sep. 6, 1988

[54] SELF ASSISTANCE TRACTION DEVICE

[76] Inventor: Kennan C. Herrick, 2160 Mastlands Dr., Oakland, Calif. 94611

[21] Appl. No.: 72,644

[22] Filed: Jul. 13, 1987

[51] Int. Cl.[4] .................................................. A61F 5/00
[52] U.S. Cl. .......................................... 128/75; 128/71
[58] Field of Search .......................... 128/75, 71, 84 R

[56] References Cited

U.S. PATENT DOCUMENTS

| | | | |
|---|---|---|---|
| 4,365,623 | 12/1982 | Wilhelm et al. | 128/75 |
| 4,489,713 | 12/1984 | Latenser | 128/75 |
| 4,593,532 | 4/1986 | Jones | 128/75 |
| 4,691,637 | 2/1987 | Rose | 128/75 |

FOREIGN PATENT DOCUMENTS

| | | | |
|---|---|---|---|
| 2414327 | 9/1979 | France | 128/75 |
| 770404 | 10/1967 | Canada | 128/75 |

*Primary Examiner*—Charles Pearson
*Assistant Examiner*—Tanya Lamb
*Attorney, Agent, or Firm*—Glen R. Grunewald; Thomas R. Lampe

[57] ABSTRACT

A device to relieve traction from a patient, the traction imposed by a weight connected to a harness on the patient through a flexible element strung over a pulley wheel, the device including a reversible motor which turns a pulley wheel mounted on a shaft through a one-way clutch, the motor being freely mounted on the shaft and raising the weight when it turns in one direction to produce slack in the flexible element, and lowering the weight to impose traction force on the patient when it turns in the reverse direction.

4 Claims, 2 Drawing Sheets

SELF ASSISTANCE TRACTION DEVICE

TECHNICAL FIELD

This invention is in the field of orthopedic traction devices that patients undergoing treatment can operate themselves to relieve or apply traction force.

BACKGROUND ART

Patients frequently require traction in treating orthopedic problems. Traction is normally applied by attaching a harness to the appropriate portion of the patient's body and connecting that harness to a weight. The force of traction produced by the weight is applied to the harness by connecting the harness to the weight with a cord that is run over a pulley positioned near the foot of the patient's bed. The vertical force produced by the weight is thereby converted to substantially horizontal force pulling on the harness.

Patients usually are not in traction continuously. It is frequently necessary or desirable to relieve traction for such purposes as having the patient change his position in bed, having the patient get out of bed, or simply relieving the force of traction for a period of time so that the patient can be more comfortable. When the patient needs to relieve the traction force it has been necessary to get assistance. A nurse or other attendant is called to lift the weight simply because the patient is unable to do it himself.

Patient's attempts at self-help to relieve the weight of traction can be difficult and even dangerous. Although some patients may be able to raise the weight by simply pulling on the cord strung over the pulley, it is difficult for the patient to hold the cord tightly while simultaneously changing position or while disengaging the cord from the harness. If the weight should fall it could produce a surge of force caused by the momentum of the weight reaching the end of the cord which would be uncomfortable or dangerous. It would also be difficult to lower the weight gently enough so that the traction force is reapplied gradually and without danger. Some patients are unable to lift the weight because they ar not strong enough or because the cord cannot be reached.

DISCLOSURE OF THE INVENTION

This invention is a self-assistance traction-relief device that can be operated by the patient to relieve traction force, to maintain relief from traction force without the patient's participation, and to reapply traction force when desired in such a gentle manner that abrupt application of force with its attendant danger is avoided. The device of this invention includes a reversible electric motor that can be operated by the patient from a remotely located switch. The device includes two circuits. One circuit causes the motor to turn in a first direction relieving traction force on the patient's body by raising the weight and a second circuit causes the motor to turn in a second direction which lowers the weight so that it gently reapplies the traction force. Details of the device and the manner of operating it are set forth in the following description of a preferred embodiment.

BEST MODE FOR CARRYING OUT THE INVENTION

Figure 2:
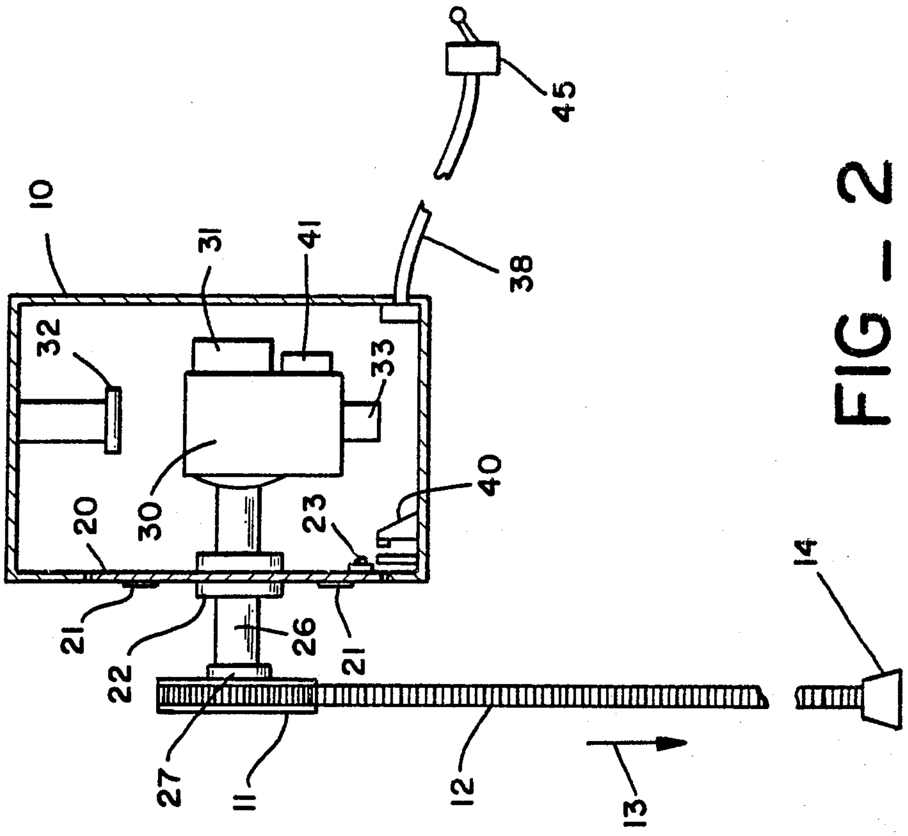
FIG. 2 is a cross-section of the device of FIG. 1 taken along the line 2—2.

The device illustrated in the drawings includes a housing 10 which includes a mounting plate 20 held to housing 10 by vertically aligned hinges 21. The plate 20 has mounted on it a pulley wheel 11 which is mounted on a shaft 26 which in turn is mounted in a bearing 22 best illustrated in FIG. 2. The pulley wheel 11 has a elongated flexible element 12 strung over it. The elongated element 12 is illustrated as a toothed tape which grips matching indentations in pulley wheel 11 to produce a mechanical interlock, all as is known to the art. Other means may be employed to prevent the elongated element 12 from slipping with respect to the pulley wheel face such as the use of a wider pulley face that the elongated element wraps around one or more times or the use of an elongated element having a conical cross-section similar to that of a "V" belt which fits in a similarly shaped pulley wheel face to provide a non-slip relationship between the belt and the pulley wheel. Elongated element 12 is connected between weight 14 and harness 15 so that a force in the direction of arrow 13 is exerted. Any suitable means for creating force in the direction of arrow 13 may be used but in this description the force producing means is weight 14.

Within the housing 10 a reversible motor 30 is freely mounted on the shaft assembly that includes shaft 26. The shaft assembly, in addition to shaft 26, may include a transmission within the housing of motor 30 to impart the appropriate speed of angular rotation and the appropriate amount of torque to shaft 26 for the function that it is to perform. The motor 30 also includes a brake element 31 that prevents rotation of the shaft 26 with respect to motor 30 when motor 30 is not operating. In other words, shaft 26 can only be turned with respect to motor 30 by the operation of motor 30; it cannot be rotated with respect to motor 30 by the force applied by weight 14. Brake 31 can be any of many brake elements known to the art and it preferably is released by the electricity used to energize motor 30 and automatically applied in the absence of such energy.

A stop 32 is mounted in housing 10. The stop works in conjunction with an extension 33 projecting from motor 30 as will be explained in more detail hereafter.

An electric switch 40 is mounted in housing 10 so that swinging of plate 20 around hinges 21, as described in more detail hereafter, will cause switch 40 to close. A biasing means 23, illustrated as a leaf spring, urges plate 20 away from switch 40. Motor 30 also has mounted on it a position-operated switch 41 such as a mercury switch. The function of switch 41 will also be described in detail hereafter.

Figure 1:
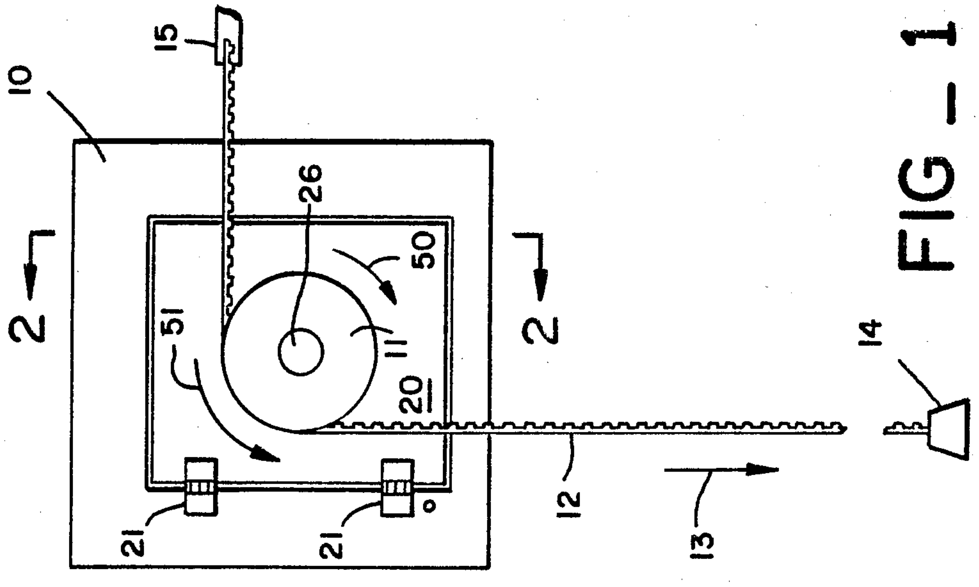
FIG. 1 is an elevation view of a device embodying this invention.

A one-way clutch mechanism 27 permits pulley wheel 11 to rotate freely with respect to shaft 26 in the direction of arrow 50 shown in FIG. 1. Arrow 50 shown in FIGS. 3 through 6 illustrates rotation in the same direction; however in FIGS. 3 through 6 the direction of rotation is viewed from behind with respect to FIG. 1. If a patient pulls harness 15 toward himself, clutch 27 will allow pulley wheel 11 to rotate freely with respect to shaft 26. However, force applied by weight 14 in the direction of arrow 13 will lock clutch 27 to prevent pulley wheel 11 from rotating with respect to shaft 26. The only way that elongated element 12 can move in the direction of arrow 13 is for shaft 26, itself, to rotate within bearing 22 in the direction indicated by arrow 51. Pulling elongated element 12 toward harness 15 and against force 13 creates a moment around the hinges 21 that causes plate 20 to rotate on hinges 21 so that the portion of plate 20 opposite the hinges swings into the housing 10 and closes switch 40. The force required to move plate 20 to a position to close switch 40 is very small, much smaller than the force required to lift weight 14.

The device is also provided with a remote switch 45, which is the two-position switch shown in FIG. 3 through 6. The two positions of switch 45 are the position shown as "A" which activates the motor to turn shaft 26 in the direction of arrow 50 and the position shown as "B" which actuates the motor to turn shaft 26 in the direction of arrow 51. Switch 45 is connected to the remainder of the circuit within housing 10 through a cable of wires 38 which is of indefinite length. Cable 38 is long enough to be conveniently operated by a patient lying in bed. The internal wiring within housing 10 is not illustrated in FIG. 2. Separate circuits to operate motor 30 in opposite directions are shown schematically in FIGS. 3, 4, 5 and 6.

Figure 3:
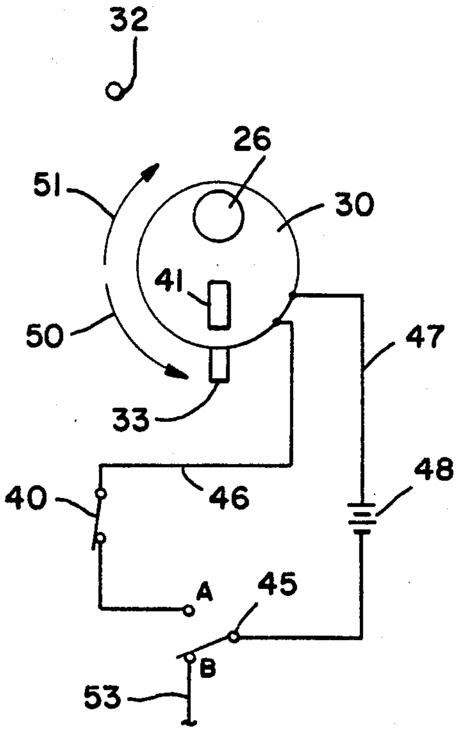
FIG. 3 is a schematic representation of a circuit useful in the device illustrated in FIG. 1 for relieving traction force.

FIG. 3 illustrates the device of this invention in a position typical of when traction force is being applied to a patient. Motor 30 is unenergized and brake 31 prevents relative rotation between motor 30 and shaft 26. Switch 40 is held closed by the force on elongated element 12 caused by resistance of harness 15. The force creates a moment around hinges 21 that swings plate 20 against switch 40. Projection 33 is shown vertical although it may be in a position rotated slightly counter clockwise from vertical. The circuit of FIG. 3 is the circuit for raising the weight 14 to relieve traction force from the patient. It includes switch 40, two-way switch 45, a power source schematically illustrated as 48 and leads 46 and 47 connected to motor 30 to cause it to turn in the direction that will cause shaft 26 to rotate in the direction of arrow 50.

Because motor 30 is freely mounted within housing 10 on shaft 26, it can turn with respect to housing 10. In the position illustrated in FIG. 3 weight 14 will apply traction force to harness 15 because shaft 26 and motor 30 are free to rotate in a clockwise direction and therefore offer no restraint to the force produced by the weight 14.

Figure 4:
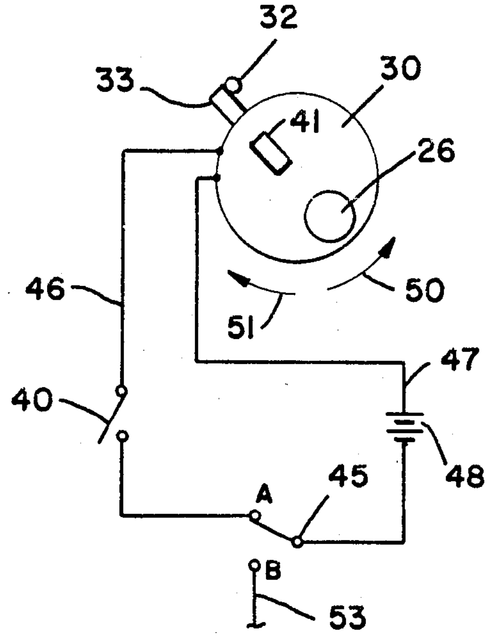
FIG. 4 illustrates the device of FIG. 3 in the position it moves to when the motor is energized.

When a patient wishes to raise weight 14 to relieve the traction force, the patient closes switch 45 by moving it to position "A" in FIG. 3 which completes the circuit illustrated in FIGS. 3 and 4 because the switch 40 is already closed as described above. With both switch 45 and switch 40 closed, a circuit to operate reversible motor 30 to turn shaft 26 in the direction of arrow 50 is activated. Motor 30, being freely mounted on shaft 26, cannot turn shaft 26 because of the force created by the weight 14 and as a result, in attempting to rotate shaft 26 in the direction of arrow 50, motor 30 itself rotates in the direction of arrow 51. Rotation in the direction of arrow 51 continues until extension 33 encounters stop 32 at which time motor 30 is no longer free to rotate in the direction of arrow 51 and shaft 26 begins to rotate in the direction of arrow 50 thereby causing pulley wheel 11 to rotate in the direction of arrow 50 in FIG. 1 to raise the weight 14 and relieve the patient from the traction force that it causes. When the force in element 12 between pulley 11 and harness 15 has been relieved, the moment moving plate 20 against switch 40 is reduced to a value at which switch 40 opens. Motor 30 then stops, brake 31 is automatically applied and weight 14 is held in position. This condition is as shown in FIG. 4. Should the patient want more slack in element 12 he can pull on the harness which causes plate 20 to swing to a position to close switch 40 which operates motor 30 until the desired amount of slack is obtained. Releasing element 12 will open switch 40 and stop motor 30, and in the stopped mode, with no traction force on harness 15, the patient is free to release elongated element 12 from harness 15 or to move himself to a more comfortable position. The entire operation is accomplished by the patient without the help of an attendant.

Figure 5:
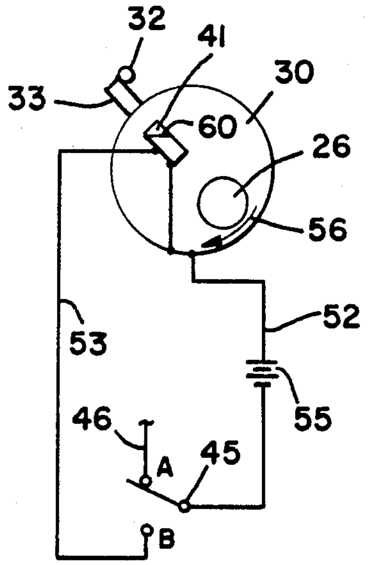
FIG. 5 is a schematic representation of a second circuit useful in the device illustrated in FIG. 1 to reapply traction force.
Figure 6:
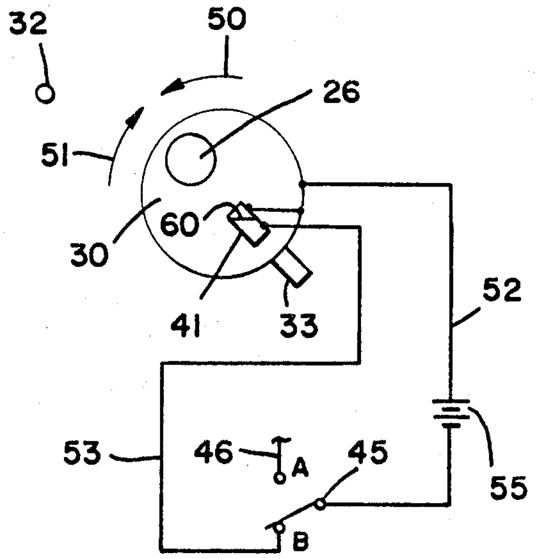
FIG. 6 illustrates the device of FIG. 5 in the position it moves to when the motor is energized.

When the patient is ready to reapply traction force a second circuit, which causes motor 30 to turn in the opposite direction, is used. The second circuit is shown in FIGS. 5 and 6. It includes the switch 45, a position-actuated switch 41 which is typically a mercury switch, a power source illustrated schematically as 55 and leads 52 and 53 connecting to motor 30.

FIGS. 5 and 6 represent, schematically, the position of the various elements of the device of this invention and the circuit used to move the elements to those positions. The circuit illustrated in FIGS. 5 and 6 is used for lowering the weight to impose traction force on a patient. FIG. 5 shows the relationship of motor 30, shaft 26, projection 33 and stop 32 as they are shown in FIG. 4, namely, with the weight raised and with slack in the elongated element 12 so that the patient does not have traction force on the harness 15. In FIG. 5 the switch 45 is in the "A" position which is the "off" position for the circuit but which is the "on" position of FIGS. 3 and 4 circuit. The weight 14 cannot be lowered because one-way clutch 27 will not permit pulley 11 to rotate in direction 51 (as shown in FIG. 1), shaft 26 cannot rotate with respect to motor 30 because brake 31 is on and motor 30 cannot rotate within housing 10 because projection 33 is in contact with stop 32. Accordingly, any slack produced in the horizontal portion of elongated element 12 as a result of the operation of the device in accordance with the description of FIGS. 3 and 4 will be maintained as long as switch 45 is in the "A" position (the off position of the circuit of FIGS. 5 and 6).

When it is desired to lower weight 14 and take up slack in elongated element 12, switch 45 is positioned in the "B" position which closes the circuit that includes positional switch 41, power source 55 and motor 30. Positional switch 41 is illustrated as a mercury switch and both electrodes of the switch are beneath the surface 60 of the mercury in FIG. 5. Upon closing the circuit, motor 30 is activated to turn shaft 26 in the direction of arrow 56. Turning shaft 26 in the direction of arrow 56 causes the shaft 26 to rotate with respect to bearing 22 because freely mounted motor 30 is held in position with projection 33 against stop 32 by the action of weight 14. By causing shaft 26 to rotate, pulley 11 rotates to lower weight 14 because both shaft 26 and the one-way clutch 27 rotate together. The weight is lowered at the rate of rotation of motor 30, which is very slow. When weight 14 is completely lowered and its full force is on harness 15, then weight 14 no longer exerts force to hold projection 33 against stop 32. As a result, motor 30 rotates with respect to shaft 26 to bring motor 30 to the position at which it is illustrated in FIG. 6. In the position illustrated in FIG. 6 at least one of the electrodes of switch 41 is no longer beneath the surface 60 of the mercury and the circuit driving motor 30 is opened, thereby cutting off power to the motor. When the force of weight 14 is on element 12 between pulley 11 and harness 15 the moment around hinges 21 causes switch 40 to close and thereby to ready the device to raise weight 14 any time the patient moves switch 45 to the "A" position.

What is claimed is:

1. A self assist traction device for relieving and applying traction force comprising:

A. a plate including a bearing;

B. a shaft mounted in said bearing to extend beyond either side of said plate;

C. a pulley wheel adapted for non-slip engagement with an elongated flexible element on one end of said shaft, said pulley wheel mounted on said shaft through one-way means to be rotatable with respect to said shaft in a direction to relieve said traction force and not rotatable with respect to said shaft in the direction to impose said traction force.

D. a freely-mounted, reversible motor mounted on the other end of said shaft to drive said shaft;

E. brake means to prevent non-driven rotation of said shaft with respect to said motor;

F. a first circuit including in series a power source, a first manually operated switch means and switch means operated by horizontal moment force exerted on said pulley wheel, said first circuit energizing said motor to turn said shaft in a direction to relieve said traction force when said moment operated switch and said manually operated switch are both closed;

G. a second circuit including in series a power source, a second manually operated switch means and a positionally operated switch means, said second circuit energizing said motor to turn said shaft in a direction to impose said traction force when said manually operated switch and said positionally operated switch are both closed, said positionally operated switch mounted to restrict the angle of rotation of said motor with respect to said plate;

H. stop means to limit rotation of said motor with respect to said plate in a direction to relieve said traction force.

2. claim 1 wherein said pulley wheel and said elongated element have interlocking elements.

3. claim 1 wherein said brake means is released by power driving said motor.

4. claim 1 wherein said first manually operated switch means and said second manually operated switch means are located remote from said motor.

* * * * *